US008967491B2

(12) United States Patent
Njatawidjaja et al.

(10) Patent No.: US 8,967,491 B2
(45) Date of Patent: Mar. 3, 2015

(54) METHOD OF TREATING TARGET SPACE, AND LIQUID PARTICLES

(75) Inventors: Ellyana Njatawidjaja, Toyonaka (JP); Timothy C Hadingham, Wallingford (GB)

(73) Assignee: Sumitomo Chemical Company, Limited, Tokyo (JP)

( * ) Notice: Subject to any disclaimer, the term of this patent is extended or adjusted under 35 U.S.C. 154(b) by 25 days.

(21) Appl. No.: 13/976,733

(22) PCT Filed: Dec. 5, 2011

(86) PCT No.: PCT/JP2011/078628
§ 371 (c)(1),
(2), (4) Date: Aug. 6, 2013

(87) PCT Pub. No.: WO2012/090683
PCT Pub. Date: Jul. 5, 2012

(65) Prior Publication Data
US 2013/0313335 A1 Nov. 28, 2013

(30) Foreign Application Priority Data

Dec. 28, 2010 (JP) .................................. 2010-293780

(51) Int. Cl.
*A01G 23/10* (2006.01)
*B05B 5/025* (2006.01)
*B05B 5/00* (2006.01)
*A61L 9/14* (2006.01)
*B01D 49/00* (2006.01)

(52) U.S. Cl.
CPC ................ *A61L 9/14* (2013.01); *B01D 49/003* (2013.01); *A61L 2202/25* (2013.01); *A61L 2209/213* (2013.01)
USPC ................ 239/3; 239/690.1; 239/708; 422/5; 422/28

(58) Field of Classification Search
USPC .......... 239/3, 337, 690, 690.1, 708; 422/5, 28
See application file for complete search history.

(56) References Cited

U.S. PATENT DOCUMENTS 4,680,163 A * 7/1987 Blidschun et al. ............... 422/28
6,592,813 B1 * 7/2003 Fox et al. ........................ 422/5

FOREIGN PATENT DOCUMENTS

| CA | 2 294 846 | 1/1999 |
| CA | 2 308 458 | 5/1999 |
| EP | 0 897 755 A2 | 2/1999 |
| EP | 1 382 399 A1 | 1/2004 |
| EP | 1 666 156 A1 | 6/2006 |
| EP | 2 246 120 A1 | 11/2010 |
| JP | 11-56195 A | 3/1999 |
| JP | 2005-013714 A | 1/2005 |
| JP | 3781873 | 3/2006 |
| JP | 3968127 B2 | 6/2007 |
| WO | WO 99/01227 A1 | 1/1999 |
| WO | WO 99/21659 | 5/1999 |
| WO | WO 03/000431 A1 | 1/2003 |
| WO | WO 2007/083164 * | 7/2007 |
| WO | WO 2007/083164 A2 | 7/2007 |
| WO | WO 2012/018141 A | 2/2012 |

OTHER PUBLICATIONS

1st Office Action received in Chinese Application No. 201180062669.8 dated Aug. 5, 2014.
International Search Report PCT/JP2011/078628 dated Mar. 20, 2012.
Written Opinion of the International Searching Authority PCT/JP2011/078628 dated Mar. 20, 2012.

* cited by examiner

*Primary Examiner* — Ryan Reis
(74) *Attorney, Agent, or Firm* — Foley & Lardner LLP

(57) ABSTRACT

According to the present invention, an arbitrary active constituent is sprayed stably so as to treat a target space. A method of the present invention, for treating a target space, includes the step of spraying, in the target space, a composition in an effective amount, the composition containing (i) a solvent and (ii) an electrolyte having a pK of not less than −10 but not more than 7, which pK is a dissociation constant with respect to water, the composition being sprayed as liquid particles in a mist form, which liquid particle have (I) an average particle diameter of not less than 100 nm but not more than 10 μm and (II) an average charge number of not less than +40 but not more than +40000.

6 Claims, No Drawings

METHOD OF TREATING TARGET SPACE, AND LIQUID PARTICLES

TECHNICAL FIELD

The present invention relates to a method of treating a target space by spraying an arbitrary active constituent stably. Further, the present invention relates to liquid particles which are suitably used in such a method.

BACKGROUND ART

In daily life, there are a lot of situations where a target object (an object to be treated) is treated by use of an arbitrary active constituent. For example, in a case where an object to be treated is an atmosphere having a bad odor in a room, providing a perfume in an atmosphere in the room is regarded as being effective to shield or get rid of the bad odor. Further, in a case where removal of microorganisms in an atmosphere is required to realize a hygienic environment, providing, in the atmosphere, a small amount of an active constituent which has activity of killing microorganisms, is regarded as being effective.

In such treatment, a preferable example of how to provide an active constituent in the atmosphere may be to spray a liquid (liquid particles in a mist form) into the atmosphere. In some cases, spraying a liquid realizes such an additional advantage that (i) liquid particles thus sprayed coagulate with dust, pollen, airborne allergens, and chemical species (such as smoke particles), and (ii) this accelerates removal of airborne contaminants from the atmosphere. A method of carrying out such treatment or a device for carrying out such treatment are disclosed in Patent Literatures 1 through 3, for example.

For example, Patent Literature 1 discloses a method of spraying, into the atmosphere, fine particles of a drug solution by use of an aerosol spray device.

Further, Patent Literature 2 discloses a method of (i) atomizing a liquid composition by use of an ultrasonic oscillator and (ii) spraying the liquid composition thus atomized.

Furthermore, Patent Literature 3 discloses another aerosol spray device having an arrangement in which, when a liquid composition is sprayed, liquid droplets (liquid composition) to be sprayed are charged by frictional electrification in a capillary tube or at an opening section via which the liquid droplets are sprayed.

CITATION LIST

Patent Literature

Patent Literature 1
Specification of Japanese Patent No. 3781873 B (Registered Date: Mar. 17, 2006)
Patent Literature 2
Japanese Patent Application Publication, Tokukai, No. 2005-13714 A (Publication Date: Jan. 20, 2005)
Patent Literature 3
Specification of Japanese Patent No. 3968127 B (Registered Date: Jun. 8, 2007)

SUMMARY OF INVENTION

Technical Problem

In view of stability in spraying a liquid composition containing an active constituent, however, the methods or devices disclosed in Patent Literatures 1 through 3 still can be improved. There has been demand for (i) a method which makes it possible to (a) spray a liquid composition stably and (b) diffuse liquid particles of the liquid composition into a larger space, and (ii) liquid particles which can be diffused in such a manner. In a case where the liquid particles can be diffused stably, it is possible to diffuse an active constituent stably, which is contained in the liquid particles. This realizes effective treatment.

The present invention is made in view of the problems. An object of the present invention is to provide a method of treating a target space by spraying liquid particles stably. Further, another object of the present invention is to provide liquid particles which are suitably used in such a treatment method.

Solution to Problem

The inventors of the present invention found, as a result of diligent study in view of the problems described above, that it is possible to diffuse a liquid composition into a large space effectively by (i) causing the liquid composition to have an appropriate charge amount and an appropriate particle diameter and (ii) spraying such a liquid composition.

That is, in order to attain the object, a method of the present invention, for treating a target space, includes the step of spraying, in the target space, a composition in an effective amount, the composition containing (i) a solvent and (ii) an electrolyte having a pK of not less than −10 but not more than 7, which pK is a dissociation constant with respect to water, the composition being sprayed as liquid particles in a mist form, which liquid particles have (I) an average diameter of not less than 100 nm but not more than 10 μm and (II) an average charge number of not less than +40 but not more than +40000.

In accordance with an embodiment of the present invention, it is preferable that an amount of the electrolyte in the composition is not less than 0.001% by mass but not more than 1% by mass with respect to a total amount of the composition.

In accordance with an embodiment of the present invention, the electrolyte is preferably at least one compound selected from the group consisting of sodium acetate, sodium hydrogen carbonate, sodium chloride, ascorbic acid, citric acid, and acetic acid.

In accordance with an embodiment of the present invention, it is preferable that the solvent is water, and an amount of the water in the composition is not less than 1% by mass but not more than 10% by mass with respect to a total amount of the composition.

In accordance with an embodiment of the present invention, it is preferable that the spraying is carried out so that an average of the number of the liquid particles thus sprayed, in a space having a volume of 1 L, is not less than 10 but not more than 1000.

In accordance with an embodiment of the present invention, it is preferable that the spraying is carried out so that the composition is electrostatically sprayed into the target space.

In accordance with an embodiment of the present invention, it is preferable that the electrostatic spraying is carried out in such a manner that (i) the composition is supplied into a spray electrode having a tube shape, (ii) a voltage is applied across the spray electrode and a discharge electrode corresponding to the spray electrode so that the composition is caused to be in a form of the liquid particles, and (iii) the composition is sprayed from the spray electrode.

Further, liquid particles of the present invention, for treating a target space, include: a solvent; and an electrolyte having a pK of not less than −10 but not more than 7, which pK is a dissociation constant with respect to water, the liquid particles having (i) an average particle diameter of not less than 100 nm but not more than 10 μm and (ii) an average charge number of not less than +40 but not more than +40000.

Advantageous Effects of Invention

According to the present invention, it is possible to provide liquid particles into an atmosphere stably. Accordingly, for example, in treatment of an atmosphere in a room, it is possible to remove effectively contaminants suspended in the atmosphere, such as dust, pollen, airborne allergens, and smoke particles.

DESCRIPTION OF EMBODIMENTS

According to a treatment method of the present embodiment, a composition is sprayed into a target space in an effective amount for treatment of the target space, which composition contains (i) a solvent and (ii) an electrolyte having a pK of not less than −10 but not more than 7, which pK is a dissociation constant with respect to water. As a method of spraying the composition, an electrostatic spray method can be suitably employed, for example.

Here, the composition is electrostatically sprayed as liquid particles in a mist form. Such liquid particles have (i) an average particle diameter of not less than 100 nm but not more than 10 μm and (ii) an average charge number of not less than +40 but not more than +40000.

According to the treatment method of the present embodiment, for example, a liquid composition (hereinafter, merely referred to as "composition" in some cases) containing an active constituent is electrostatically sprayed as liquid particles in a mist form, which liquid particles have (i) an appropriate charge amount and (ii) an appropriate particle diameter. With the arrangement, it is possible to treat a target space by diffusing the active constituent in the target space effectively.

Here, according to the present invention, the "target space" is a space which is treated in such a manner that liquid particles are sprayed into the space. Note that the active constituent is not necessarily contained in the composition. It is possible that the composition does not contain such an active constituent. The following description deals with each of elements of the liquid composition.

<Liquid Composition>

As described above, the composition sprayed in accordance with the treatment method of the present embodiment contains at least (i) a solvent and (ii) an electrolyte which has been dissolved in the solvent.

(Solvent)

The composition used in the treatment method of the present embodiment can be prepared with the use of a solvent which is in a liquid form at room temperature. Here, according to the present invention, the "room temperature" is a temperature of not less than 5° C. but not more than 35° C., i.e., a range of 20° C.±15° C. (which is defined by JIS Z 8703 (standard atmospheric conditions for testing)). Examples of the solvent which can be used in the treatment method of the present embodiment encompass the following compounds.

That is, examples of such a solvent encompass ethanol, dipropylene glycol ethyl ether, dipropylene glycol-n-propyl ether, dipropylene glycol-n-buthyl ether, tripropylene glycol methyl ether, tripropylene glycol ethyl ether, tripropylene glycol-n-propyl ether, dimethyl glutarate, dimethyl adipate, propylene glycol, triethylene glycol, glycerine, polyethylene glycol, polypropylene glycol, dipropylene glycol methyl ether, propylene glycol methyl ether, tripropylene glycol methyl ether, 1-methoxy-2-propanol acetic acid ether, 1-butoxy-2-propanol, 1-propoxy-2-acetoxy propane, and oxybis (methoxy)propane. Among these, dipropylene glycol-n-propyl ether, dimethyl glutarate, and dimethyl adipate are particularly preferable.

Specific examples of such a solvent further encompass liquid paraffin, squalane, squalene, isopropyl myristate, cetyl myristate, octyldodecyl myristate, isopropyl palmitate, butyl stearate, stearyl stearate, ethyl oleate, decyl oleate, diethyl sebacate, pentaerythrithyl tetraoctanoate, glycol distearate, octyl palmitate, octyl stearate, isononyl isononanoate, isotridecyl isononanoate, 2-ethylhexyl palmitate, cetyl 2-ethylhexanoate, isostearyl myristate, neopentyl glycol di-2-ethylhexanoate, neopentyl glycol dicaprate, glyceryl tri(2-ethylhexanoate), caprylic/capric triglyceride, glyceryl triisostearate, trimethylolpropane triisostearate, pentaerythritol tetra 2-ethylhexanoate, pentaerythritol tetraisostearate, diglyceryl tetraisostearate, octyldodecyl lactate, diisostearyl malate, polyglyceryl monoisostearate, polyglyceryl diisostearate, diglyceryl triisostearate, polyglyceryl triisostearate, polypropylene glycol oligo ester succinate, ditrimethylolpropane oligo ester iso stearate/sebacate, ditrimethylolpropane triethylhexanoate, coconut oil, palm oil, olive oil, jojoba oil, dimethyl silicone oil, highly-polymerized dimethyl silicone oil, cyclic silicone oil, polyether modified silicone oil, amino modified silicone oil, and methylphenyl silicone oil.

Further, the composition can contain water of not less than 1% by mass but not more than 10% by mass with respect to an amount of the composition, which water is suitably used when the electrolyte (later described) is added to the composition. In a case where the composition contains water in the above range, it is possible to cause the electrolyte to be dissolved in the composition successfully. This makes it possible to provide the composition in the atmosphere as stable liquid particles.

(Electrolyte)

The composition used in the treatment method of the present embodiment contains an electrolyte of not less than 0.001% by mass but not more than 1% by mass with respect to a total amount of the composition, which electrolyte having a pK of not less than −10 but not more than 7, which pK is a dissociation constant in a case where the electrolyte is dissolved in water. In a case where the composition contains the electrolyte, it is possible to cause easily liquid particles of the composition to be in a desired charge state when the composition is sprayed. In a case where an amount of the electrolyte in the composition is less than 0.001% by mass, the liquid particles are unlikely to be charged. Further, in a case where the amount of the electrolyte in the composition is more than 1% by mass, the liquid particles are charged excessively. Accordingly, in a case where the amount of the electrolyte in the total amount of the composition is not less than 0.001% by mass but not more than 1% by mass, it becomes possible to (i) cause the liquid particles to be in a desired charge state easily and (ii) provide the liquid particles stably. Note that it is preferable that the dissociation constant pK of the electrolyte is in a range of −5 to 6.

The electrolyte added to the composition may be in a form of an aqueous solution. Preferable examples of the electrolyte encompass sodium acetate, sodium hydrogen carbonate, sodium chloride, ascorbic acid, citric acid, and acetic acid.

(Active Constituent)

The composition used in the treatment method of the present embodiment may contain an active constituent. According to the present invention, the "active constituent" is a component which is effective in treating a target space. It is possible to (i) select, as the active constituent, an arbitrary component in accordance with an object and (ii) cause the composition to contain the component thus selected. Preferable examples of such an active constituent encompass a perfume and an air-cleaning agent.

It is preferable that the composition used in the treatment method of the present embodiment contains an active constituent in an amount of not less than 0.05% by mass but not more than 44.5% by mass with respect to a total amount of the composition.

(Perfume)

The perfume, contained, as the active constituent, in the composition used in the treatment method of the present embodiment, may be an essential oil or another fragrance oil, for example. As the perfume, it is possible to use only a part of all fractions (oil components) contained in such an oil.

More specifically, preferable examples of such a perfume encompass Melaleuca oil, tea tree oil (such as terpinene-4-ol), catmint oil (such as *Nepeta Cateria* and a refined oil of *Nepeta Cateria*), a fraction of catmint oil (such as a fraction containing nepetalactone), *thymus* oil (such as an oil of *Thymus Vulgaris*), and a fraction of *thymus* oil (such as a fraction containing thymol).

Further, a perfume such as a fragrance oil is typically, for example, (i) a mixture of different sorts of compound, whose backbones are different from each other in chain length, or (ii) a mixture containing different sorts of stereoisomeric form. It is possible to use such a fragrance oil as the active constituent of the present embodiment.

Among the examples described above, the perfume preferably includes a refined oil of at least one sort selected from the group consisting of tea tree oil, catmint oil, and *Thymus* oil.

In a case where the composition used in the treatment method of the present embodiment contains a fragrance oil, it is preferable that an amount of the fragrance oil in the composition is not less than 5% by mass but not more than 35% by mass. Further, in a case where (i) the composition contains at least two active constituents, and (ii) one of them is a fragrance oil, it is preferable that an amount of the fragrance oil with respect to a total amount of all the active constituents is not less than 55% by mass but not more than 95% by mass, more preferably, not less than 57.5% by mass but not more than 92% by mass.

(Air-Cleaning Agent)

The composition used in the treatment method of the present embodiment can contain an air-cleaning agent as an active constituent. Specific examples of the air-cleaning agent that can be used in the composition encompass an active air-cleaning component, an active antibacterial component, an active antifungal component, and an active antiallergenic component.

Here, the "active air-cleaning component" is a substance having deodorizing activity.

Furthermore, the "active antibacterial component" is a substance having inhibiting activity of bacterial growth.

Moreover, the "active antifungal component" is a substance having inhibiting activity of fungal growth.

Further, the "active antiallergenic component" is a substance having inhibiting activity of growth of an allergen(s).

As the air-cleaning agent of the present embodiment, it is possible to use either (i) a substance which develops a single function among the functions described above or (ii) a substance which is expected to develop a plurality of functions among the functions described above. Specifically, preferable examples of the substance which is expected to develop, as the air-cleaning agent, such plurality of functions, encompass a polyhexamethylene bi-guanido polymer, a polyhexamethyl guanido polymer, alkyl dimethyl benzyl ammonium chloride, octyl decyl dimethyl ammonium chloride, chlorhexidine, chlorhexidine digluconate, benzalkonium chloride, sodium hypochlorite, 2-phenylphenol, polyethylene glycol 300, 2-benzyl-4-chlorophenol, 2-phenoxyethanol, glutaraldehyde, phthalaldehyde, chloroxylenol, trichlorophenol, phenol, silver salt (particularly, water-soluble silver salt), hexachlorophene, peracetic acid, lactic acid, performic acid, potassium permaganate, and potassium peroxymonosulfate.

In a case where (i) the composition used in the treatment method of the present embodiment contains an air-cleaning agent as an active constituent and (ii) the air-cleaning agent is not an electrolyte (the air-cleaning agent which does not function as the electrolyte of the present invention), it is preferable that an amount of the air-cleaning agent in the composition is not less than 0.05% by mass but not more than 20% by mass, more preferably, not less than 0.1% by mass but not more than 17% by mass, further more preferably, not less than 0.1% by mass but not more than 15% by mass. In a case where the air-cleaning agent is an electrolyte (the air-cleaning agent which functions as the electrolyte of the present invention), an amount of the air-cleaning agent in the composition is not less than 0.001% by mass but not more than 1% by mass.

Examples of the active air-cleaning component encompass tannin, polyphenol (such as flavonoid (e.g., chalkone, flavanone, flavanol, flavone, flavonol, or isoflavone)), cyclodextrin, lauryl methacrylate, geranyl clorinate, 4-hydroxy-6-methyl-3-(4-methylpentanoyl)-2-pyrone, formalin, glyoxal, sodium bisulfite, sodium sulfite, dihydroxyacetone, 3,5,5-trimethyl hexanol, β-ethoxy propionaldehyde, glutaraldehyde, methacrylate ester, maleic acid ester, maleic acid monoamide, maleic acid imide, fumaric acid ester, β-acyl acrylic acid, salt of β-acyl acrylic acid, senecioic acid citronellyl, 1,3-pentadiene-1-calboxylic acid alkyl ester, pinane hyderoperoxide, p-cymeneperoxide, 1,2-propyleneoxide, 1,2-butyleneoxide, glycidyl ether, saccharose octaacetate, Fe(III)-octacarboxyphthalocyanine, Fe(III)-tetracarboxyphthalocyanine, 5-methyl-2-isopropyl-2-hexenol, p-butoxyphenol, catechol, hydroquinone, 4-methylcatechol, 1,2,4-trihydroxybenzene, 3-methylcatechol, 3-methoxycatechol, carnosol, rosmanol, brazilin, hematoxylin, shikonin, myricetin, bicalein, bicalin, citral, vanilline, and coumarin.

Examples of the active antibacterial component encompass triclosan, trichlorocarbanilide, isopropylmethylphenol, N-(dichloro fluoromethylthio)-phthalamide, N'-(dichloro fluoromethylthio) N,N'-dimethyl-N'-phenyl-sulphamide, polyoctyl polyaminoethylglycine, thiabendazole, chlorine dioxide, 2-bromo-2-nitroethanol, 2-bromo-2-nitropropane-1,3-diol, 2-bromo-2-nitropropanol, 1-bromo-1-nitro propanol, 1,4-dibromo-1,4-dinitro butanediol-2,3-cetylpyridinium, 1-bromo-1-nitro-2-methyl propanol-2-cetylpyridinium, cetylpyridinium chloride, benzethonium chloride, acrinol, povidone-iodine, mercurochrome, chloramphenicol, fradiomycin sulfate, gentamycin sulfate, oxytetracycline hydrochloride, polymyxin B sulfate, trichomycin, and griseofulvin.

Examples of the active antifungal component encompass benzoic acid, salt of benzoic acid, sorbic acid, salt of sorbic acid, paraoxybenzoic esters, sodium dehydroacetate, propionic acid, polylysine, thiabendazole, terpene alcohol (such as linalool, geraniol, nerol, citronellol, α-terpineol, terpinene-4-ol, and isopulegol), $C_7$ to $C_{15}$ alicyclic alcohol (such as 2,4-dimethyl-3-cyclohexene-1-methanol, 4-isopropylcyclohexanol, 4-isopropylcyclohexanemethanol, 1-(4-isopropylcyclohexyl)-ethanol, and 2,2-dimethyl-3-(3- methylphenyl)-propanol), and $C_7$ to $C_{15}$ arylalkyl alcohol (or $C_7$ to $C_{15}$ alkylaryl alcohol) (such as benzyl alcohol, phenylethyl alcohol, phenyl propyl alcohol, carvacrol, and eugenol).

Examples of the active antiallergenic component encompass hydroxyapatite, epicatechin, epigallocatechin, epicatechin gallate, epigallocatechin gallate, gallic acid, and an ester compound of gallic acid and $C_1$ to $C_4$ alcohol.

Further, other than the above examples, the air-cleaning agent may be any component described in (i) "1-Human hygiene biocidal products", (ii) "2-Private area and public health area disinfectants and other biocidal products", and (iii) "3-Veterinary hygiene biocidal products" (List of participants and of applicants having submitted a dossier in accordance with Article 5(3) of Regulation (EC) No. 2032/2003 (by product-types)).

It is preferable that the active constituent serves as an electrolyte contained in a composition to be sprayed. Examples of the active constituent that also serves as the electrolyte encompass salt of quaternary amine, a preservation agent, and salt of chlorhexidine (such as chlorhexidine digluconate). Such an active component can also serve as the electrolyte. Accordingly, it is possible to cause the composition to contain (i) only such an active constituent or (ii) such an active component and the electrolyte(s) described above in combination with each other.

As to the active constituents described above, it is possible to use only one sort of active constituent or two or more sorts of active constituent in combination with each other. In a case where two or more sorts of active constituent are used, it is possible to use, for example, (i) only two or more sorts of perfume in combination with each other, (ii) only two or more sorts of air-cleaning agent in combination with each other, (iii) only two or more sorts of pesticide (or insect repellent) in combination with each other, or (iv) one or more sorts of perfume, one or more sorts of air-cleaning agent, and one or more sorts of pesticide (or insect repellent) in combination with each other.

Note that, other than the electrolyte, the solvent, and the active constituent, the composition can further contain, if necessary, a surface tension control component as an arbitrary component. The surface tension control component is added to the composition so that the composition to be sprayed has physical characteristics (an average particle diameter of liquid particles, and an average charge number) in the respective desired ranges described above.

Examples of the surface tension control component encompass isoparaffin (e.g., Isopar L), and silicone oil (such as decamethyltetrasiloxane, decamethylcyclopentasiloxane, dodecamethylcyclohexasiloxane, and a mixture of these). It is possible to use only one sort of surface tension control component or two or more sorts of surface tension control component.

Further, it is possible to add a surfactant to the composition as the surface tension control component. Examples of a nonionic surfactant encompass sorbitan fatty acid ester (such as sorbitan stearate, and sorbitan oleate), glycerin fatty acid ester (such as glyceryl stearate, glyceryl isostearate, glyceryl oleate, polyglyceryl stearate, polyglyceryl isostearate, and polyglyceryl oleate), polyoxyethylene alkyl ether (such as polyoxyethylene lauryl ether, polyoxyethylene cetyl ether, polyoxyethylene stearyl ether, polyoxyethylene oleyl ether, and polyoxyethylene styrylphenyl ether), polyoxyethylene sorbitan fatty acid ester (such as polyoxyethylene sorbitan coconut oil fatty acid, polyoxyethylene sorbitan oleate, and polyoxyethylene sorbitan stearate), and polyoxyethylene sorbitol fatty acid ester (such as polyoxyethylene sorbitol tetraoleate). Other than these, the nonionic surfactant may be polyoxyethylene hydrogenated castor oil, alkylphenol polyglycol ether, or the like. Examples of an ampholytic surfactant encompass betaine (such as lauryl betaine, and stearyl betaine), and imidazoline derivatives (such as di-sodium N-lauryl-p-iminodipropionate). Other than these, the ampholytic surfactant may be lecithin or the like. Examples of an anionic surfactant encompass alkyl sulfate (such as sodium lauryl sulfate and triethanolamine lauryl sulfate), polyoxyethylene alkyl ether sulfate such as (sodium polyoxyethylene lauryl ether sulfate and triethanolamine polyoxyethylene lauryl ether sulfate), alkylbenzene sulfonate (such as sodium dodecylbenzene sulfonate), and polyoxyethylene alkyl ether phosphate (such as sodium dipolyoxyethylene lauryl ether phosphate, and sodium dipolyoxyethylene oleyl ether phosphate). Examples of a cationic surfactant encompass alkyl ammonium salt (such as cetyltrimethylammonium chloride and distearyldimethylammonium chloride).

In a case where the composition used in the treatment method of the present embodiment contains a surface tension control component, it is preferable that a minimum value of an amount of the surface tension control component in the composition is 0.5% by mass. Further, it is preferable that a maximum value of an amount of the surface tension control component in the composition is 10% by mass. It is preferable that the amount of the surface tension control component is in a range of the minimum value to the maximum value.

Other than the electrolyte, the solvent, the active constituent, and the surface tension control component, the composition used in the treatment method of the present embodiment can contain another component.

The "another component" may be a viscosity control component. For example, it is possible to increase the composition in viscosity by adding polyethylene glycol or glycerine to the composition.

<Treatment Method>

According to the treatment method of the present embodiment, the liquid composition is electrostatically sprayed as liquid particles in a mist form, so as to treat a target space, which liquid particles have an average particle diameter of not less than 100 nm but not more than 10 µm and an average charge number of not less than +40 but not more than +40000. Here, the sign "+" of the average charge number indicates positive charge.

Note that, according to the present invention, the "average particle diameter" is a value which is obtained by measurement carried out by use of "Aero Particle Sizer Model 3321 (manufactured by TSI Instruments Inc.) or "Scanning Mobility Particle Sizer Model 3936 (manufactured by TSI Instruments Inc.). Note that, for liquid particles having an average particle diameter of not less than 100 nm but not more than 500 nm (i.e., 0.5 µm), the value obtained by use of Model 3936 was used. Meanwhile, for liquid particles having an average particle diameter of more than 0.5 µm but not more than 10 µm, the value obtained by use of Model 3321 was used.

Further, according to the present invention, the "average charge number" is a value which is obtained by measurement carried out by use of "Aerosol Electrometer Model 3068B (manufactured by TSI Instruments Inc.) or "Faraday Cup System" (manufactured by Tectra Physical Instruments GmbH.). Note that, for liquid particles having an average particle diameter of not less than 100 nm but not more than 5000 nm (i.e., 5 µm), the average charge number was obtained by use of Aerosol Electrometer Model 3068B. For liquid particles having an average particle diameter of more than 5 µm but not more than 10 µm, the average charge number was obtained by use of Faraday Cup System.

In a case where the liquid particles have an average particle diameter of more than 10 μm, the liquid particles are likely not to be diffused into the atmosphere but to fall on the ground. On the other hand, in a case where the liquid particles have an average particle diameter of less than 100 nm, the liquid particles cannot be diffused into the atmosphere efficiently.

Further, in a case where the liquid particles have an average charge number of more than +40000, it becomes difficult to maintain the form of liquid particles stably. On the other hand, in a case where the liquid particles have an average charge number of less than +40, the liquid particles cannot be diffused into the atmosphere efficiently.

According to the treatment method of the present embodiment, it is preferable to spray the liquid particles in a target space so that an average of the number of the liquid particles in a space (atmosphere) having a volume of 1 L is not less than 10 but not more than 1000. The spraying can be carried out either intermittently or continuously. Note that a volume of 1 L is a volume obtained at room temperature which is defined as described above.

According to the present Specification and Claims described below, the number of the liquid particles can be measured, for example, by use of "Aerodynamic Particle Sizer Model 3321 (manufactured by TSI Instruments Inc.)" or "Scanning Mobility Particle Sizer Model 3936 (manufactured by TSI Instruments Inc.).

The number of the liquid particles is an average of the number of the liquid particles existing in a target space in a chamber, which number is obtained under a condition where the liquid particles are sprayed, for not less than 10 seconds, into the chamber having a maximum volume of 120 m$^3$. According to the present Specification, the liquid particles are sprayed into a chamber having a volume of 5.8 m$^3$ for not less than 10 seconds, and an average particles number is measured after 30 seconds elapse since the spraying is finished.

For example, in a case where the liquid particles of the present embodiment contain an active constituent, it is preferable to spray the liquid particles in a target space so that, for at least 30 seconds in a time period from 1 minute after the spraying is finished to 120 minutes after the spraying is finished, an average of the number of liquid particles in a space having a volume of 1 L is kept to be not less than 10 but not more than 1000. In this case, it is possible to cause the active constituent to function effectively. Accordingly, it is possible to treat the target space. The liquid particles of the present embodiment can float stably in the target space from 30 seconds after the spraying is finished to a couple of hours after the spraying is finished. Accordingly, in a case where such an average of the number of the liquid particles in the target space is in the predetermined range at a time 30 seconds after the spraying is finished, it is possible to carry out desired treatment.

Here, an amount of the liquid composition to be applied to the target space is in a rage of 0.1 g to 10 g per day for a space having a volume of 120 m$^3$. In a case where the liquid composition is caused to exist in the target space for a predetermined time period, it is possible to treat the target space effectively.

The treatment of the target space can be carried out, for example, in such a manner that the composition is sprayed from a spray device in an atmosphere (i.e., the target space).

According to the present embodiment, the composition is electrostatically sprayed in a target space. An electrostatic spray device is suitably used to carry out such electrostatic spraying. For example, (i) a spray device which includes a spray electrode to which the composition is supplied, and a reference electrode (discharge electrode) provided in the vicinity of the spray electrode is employed, and (ii) the composition is sprayed from the spray device in the form of liquid particles in such a manner that an electric field is generated by application of a voltage across the spray electrode and the reference electrode. The voltage thus applied is preferably not less than 1 kV but not more than 30 kV.

Such an electrostatic spray device sprays the composition in such a manner that (i) the composition is supplied to the spray electrode, (ii) the spray electrode is ultimately exposed to an electric field (potential difference) formed between the spray electrode and the reference electrode, (iii) this causes the composition to be charged, and, as a result, (iv) the composition is made into liquid particles and is sprayed. Such an electrostatic spray device has been well known in this field (see Sir Geoffrey Taylor, "Proceedings of the Royal Society-1964, p. 383-397", for example).

According to the treatment method described above, the liquid particles are successfully charged with the electrolyte dissolved in the composition. It becomes therefore possible to spray the composition effectively. Accordingly, it is possible to provide the liquid particles into an atmosphere (i.e., a target space) stably, and diffuse the liquid particles into a large space effectively. For example, in a case where the composition contains an active constituent, it is possible to diffuse the active constituent effectively.

Further, such liquid particles can exist in the atmosphere (i.e., the target space) stably for a long time, and can be diffused into a large space effectively.

EXAMPLES

The present invention is described below more specifically with a specific example. Note, however, that the present invention is not limited to the following Example.

Example 1

First, a composition to be sprayed was prepared, which composition was constituted as shown in Table 1.

TABLE 1

| | |
|---|---|
| Fragrance oil 225696 (produced by Firmenich International SA) | 30% by mass |
| Dipropyleneglycol monomethyl ether | 61% by mass |
| Isoparaffin (Isopar L) | 6% by mass |
| Water | 2.988% by mass |
| Sodium acetate | 0.012% by mass |

Next, a spray device for forming liquid particles was manufactured as described below. First, a polypropylene plate which was a dielectric material was caused to have two holes. Then, a capillary (made from stainless steel, external diameter: 0.4 mm, internal diameter: 0.2 mm, length: 18 mm) for spraying liquid particles and a pin (made from stainless steel, external diameter: 0.55 mm, length: 14 mm) were provided through the holes, respectively, so as to be parallel to each other. A distance between the capillary and the pin was 8 mm. Here, the capillary and the pin were provided not to project from a surface of the polypropylene plate. Further the capillary and the pin were provided so that the polypropylene plate which was the dielectric material was positioned between the capillary and the pin which were parallel to each other.

Next, the capillary serving as a spray electrode having a tube shape and the pin serving as a discharge electrode were connected to an electrical drive circuit electrically. Further, one of the ends of the capillary (on a back surface side of the polypropylene plate) was connected to a container in which the composition was provided, which composition was to be in a form of liquid particles. This makes it possible to provide the composition into the capillary. The spray device was thus manufactured.

The electrical drive circuit included a battery of 3 V, a control switch, and a high voltage converter. The high voltage converter was capable of generating a voltage of 5 kV across the capillary and the pin.

In a case where a voltage of 5 kV was applied across the capillary and the pin by driving the electrical drive circuit, liquid particles were emitted from the other one of the ends of the capillary (on a main surface side of the polypropylene plate).

The spray device was placed inside a chamber having a height of 1.8 m and a target space of 5.8 m$^3$. Inside the chamber, the spray device was positioned along an inner wall at a height of 1.2 m from a bottom surface (a bottom surface of the chamber). Then, the composition was sprayed in the form of liquid particles for 3 minutes so that a total of 73 mg of the liquid particles was spread over the entire target space (73 mg/5.8 m$^3$, 3 minutes). 30 seconds after the spraying was finished, sampling was carried out at a position in the chamber, which position was 1.34 m away from the spray device and at a height of 1 m from the bottom surface. Then, by use of Aerodynamic Particle Sizer Model 3321, the liquid particles thus sprayed were measured in average particle diameter and in the number of liquid particles in a space (atmosphere) having a volume of 1 L. Further, the liquid particles thus sprayed were measured in average charge number by use of Aerosol Electrometer Model 3068B. The results were described below.

Moreover, a time period (a time period from a time when the liquid particles were sprayed to a time when treatment of the target space was completed) necessary for the active constituent (i.e., the liquid particles containing the active constituent) to be spread over the target space in the chamber was measured. Specifically, the time period was measured in such a manner that (i) an observer stood, in the chamber, along another inner wall (opposite inner wall) (1.8 m away from the spray device) facing the inner wall along which the spray device was positioned, and (ii) a time period from a time when the liquid particles were sprayed to a time when the observer detected a scent was measured. The result was described below.

Average particle diameter: 0.6 μm
    Average charge number: +1500
    The number of liquid particles in a space having a volume of 1 L: 20
    Time period necessary for active constituent to be spread over target space: 15 seconds Industrial Applicability According to the present invention, it is possible to provide liquid particles in an atmosphere stably. Accordingly, the present invention is effective as a treatment method for treating a target space, e.g., removing efficiently contaminants floating in an atmosphere in a room, such as dust, pollen, airborne allergens, and smoke particles.

The invention claimed is:

1. A method of treating a target space, comprising the step of:
spraying, in the target space, a composition in an effective amount,
the composition containing (i) a solvent, (ii) an electrolyte having a pK of not less than −10 but not more than 7, which pK is a dissociation constant with respect to water, and (iii) an active constituent,
the composition being sprayed as liquid particles in a mist form, which liquid particles have (I) an average diameter of not less than 100 nm but not more than 10 μ and (II) an average charge number of not less than +40 but not more than +40000, and
the composition being sprayed as liquid particles so that, for at least 30 seconds in a time period from 1 minute after the spraying is finished to 120 minutes after the spraying is finished, an average of the number of the liquid particles in a space having a volume of 1 L is kept to be not less than 10 but not more than 1000.

2. The method as set forth in claim 1, wherein:
an amount of the electrolyte in the composition is not less than 0.001% by mass but not more than 1% by mass with respect to a total amount of the composition.

3. The method as set forth in claim 1, wherein:
the electrolyte is at least one compound selected from the group consisting of sodium acetate, sodium hydrogen carbonate, sodium chloride, ascorbic acid, citric acid, and acetic acid.

4. The method as set forth in claim 1, wherein:
the solvent is water; and
an amount of the water in the composition is not less than 1% by mass but not more than 10% by mass with respect to a total amount of the composition.

5. The method as set forth in claim 1, wherein:
said spraying is carried out so that the composition is electrostatically sprayed into the target space.

6. The method as set forth in claim 5, wherein:
said electrostatic spraying is carried out in such a manner that
(i) the composition is supplied into a spray electrode having a tube shape,
(ii) a voltage is applied across the spray electrode and a discharge electrode corresponding to the spray electrode so that the composition is caused to be in a form of the liquid particles, and
(iii) the composition is sprayed from the spray electrode.

* * * * *